(12) United States Patent
Lee

(10) Patent No.: US 12,569,800 B2
(45) Date of Patent: Mar. 10, 2026

(54) FLUID TREATMENT APPARATUS

(71) Applicant: SEOUL VIOSYS CO., LTD., Ansan-si (KR)

(72) Inventor: Chung Hoon Lee, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 407 days.

(21) Appl. No.: 18/026,123

(22) PCT Filed: Sep. 16, 2021

(86) PCT No.: PCT/KR2021/012718
§ 371 (c)(1),
(2) Date: Mar. 14, 2023

(87) PCT Pub. No.: WO2022/060132
PCT Pub. Date: Mar. 24, 2022

(65) Prior Publication Data
US 2023/0347280 A1     Nov. 2, 2023

Related U.S. Application Data

(60) Provisional application No. 63/079,076, filed on Sep. 16, 2020.

(51) Int. Cl.
*B01D 46/00*     (2022.01)
*A61L 9/14*      (2006.01)
(Continued)

(52) U.S. Cl.
CPC .......... *B01D 53/1431* (2013.01); *A61L 9/145* (2013.01); *A61L 9/20* (2013.01);
(Continued)

(58) Field of Classification Search
CPC ...... B01D 47/00; B01D 47/02; B01D 47/022; B01D 46/0028
See application file for complete search history.

(56) References Cited

FOREIGN PATENT DOCUMENTS

| | | | | |
|---|---|---|---|---|
| CN | 208678770 U | * | 4/2019 | |
| CN | 110090513 A | * | 8/2019 | ............. B01D 53/74 |

(Continued)

OTHER PUBLICATIONS

International Search Report dated Jan. 7, 2022 in International Application No. PCT/KR2021/012718 (with English Translation).
(Continued)

*Primary Examiner* — Robert A Hopkins
(74) *Attorney, Agent, or Firm* — Oblon, McClelland, Maier & Neustadt, L.L.P.

(57)            ABSTRACT

A fluid treatment device including: a pipe having an inlet through which fluid is introduced into the pipe from a fluid treatment space, an outlet through which sterilized fluid is discharged to the fluid treatment space, and a flow channel connecting the inlet to the outlet, the pipe providing a sterilization area in the flow channel; a solvent filling at least a portion of the sterilization area; and at least one light source module disposed in the sterilization area, and including a light source to emit sterilizing light and a substrate on which the light source is mounted, in which the fluid introduced through the inlet passes through the solvent towards the outlet, the solvent traps contaminants contained in the fluid when the fluid passes through the solvent, and the light source module sterilizes the solvent with the contaminants trapped therein.

18 Claims, 8 Drawing Sheets

(51) Int. Cl.

| | | |
|---|---|---|
| *A61L 9/20* | (2006.01) | |
| *B01D 47/02* | (2006.01) | |
| *B01D 53/14* | (2006.01) | |
| *C02F 1/32* | (2023.01) | |

(52) U.S. Cl.

CPC ......... *B01D 46/0028* (2013.01); *B01D 47/02* (2013.01); *B01D 47/022* (2013.01); *C02F 1/325* (2013.01); *A61L 2209/14* (2013.01); *B01D 2257/91* (2013.01); *B01D 2258/06* (2013.01); *B01D 2273/30* (2013.01); *B01D 2279/65* (2013.01); *C02F 2201/3227* (2013.01); *C02F 2201/3228* (2013.01); *C02F 2201/328* (2013.01); *C02F 2303/04* (2013.01)

(56)     References Cited

FOREIGN PATENT DOCUMENTS

| | | | |
|---|---|---|---|
| CN | 209934340 U | * | 1/2020 |
| JP | 2003-322371 | | 11/2003 |
| JP | 2011-206123 | | 10/2011 |
| KR | 10-2005-0009448 | | 1/2005 |
| KR | 10-2010-0003662 | | 1/2010 |
| KR | 10-2015-0061810 | | 6/2015 |
| KR | 10-2056943 | | 12/2019 |

OTHER PUBLICATIONS

Written Opinion dated Jan. 7, 2022 for International Patent Application No. PCT/KR2021/012718.

* cited by examiner

【FIG. 1】
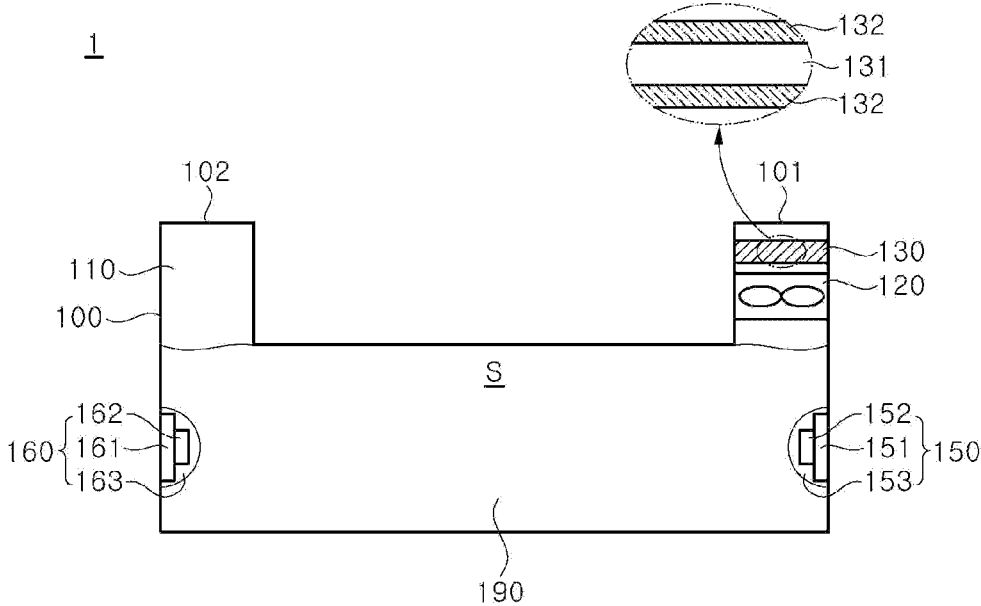
【FIG. 2】
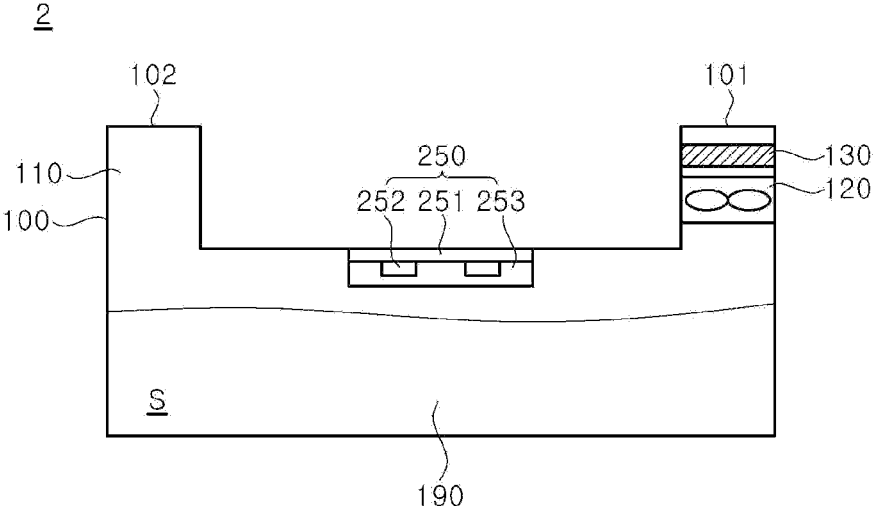

【FIG. 3】
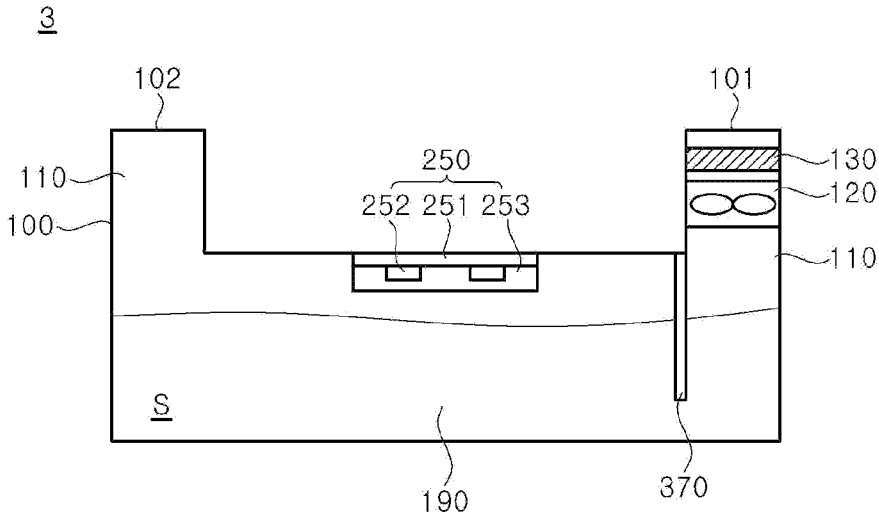
【FIG. 4】
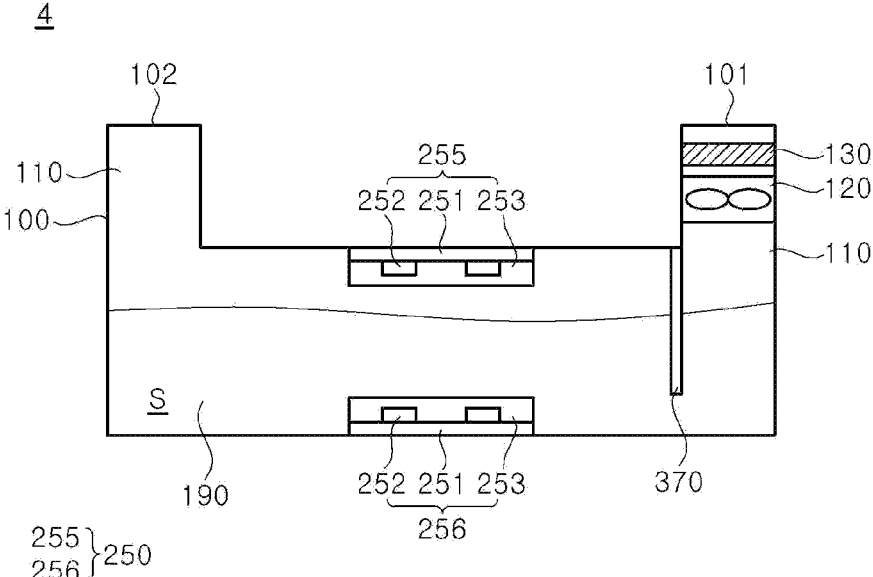

【FIG. 5】
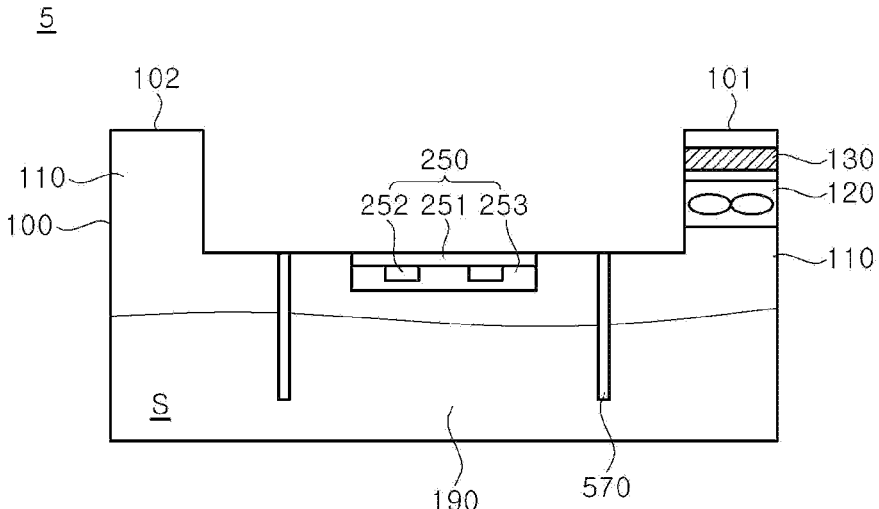
【FIG. 6】
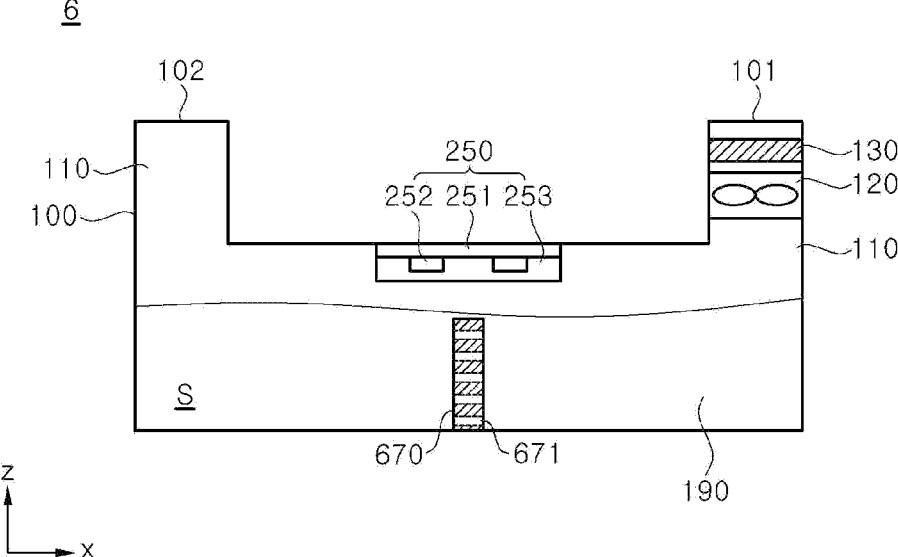

【FIG. 7】
<u>6</u>
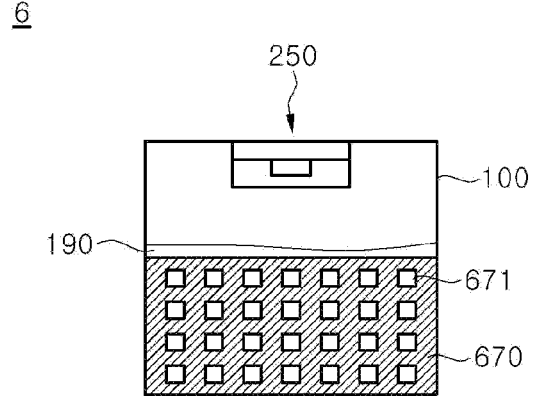
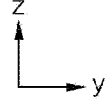
【FIG. 8】
<u>7</u>
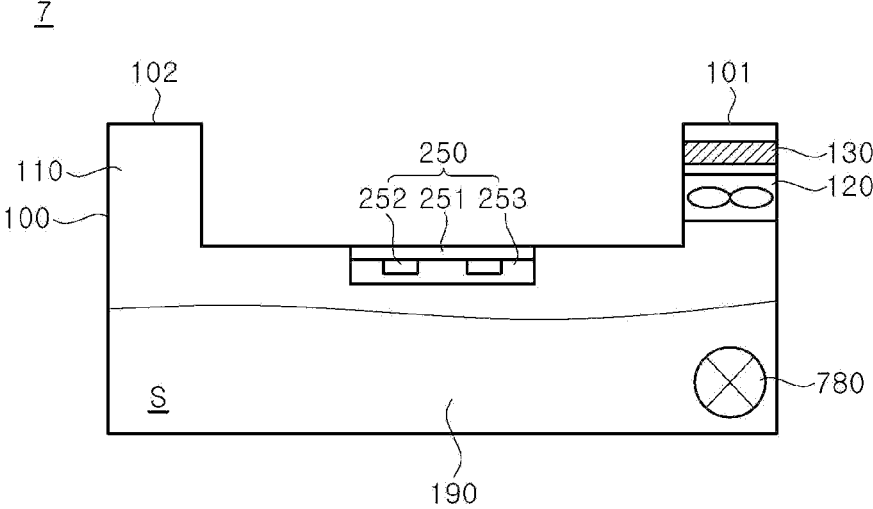

【FIG. 9】
<u>8</u>
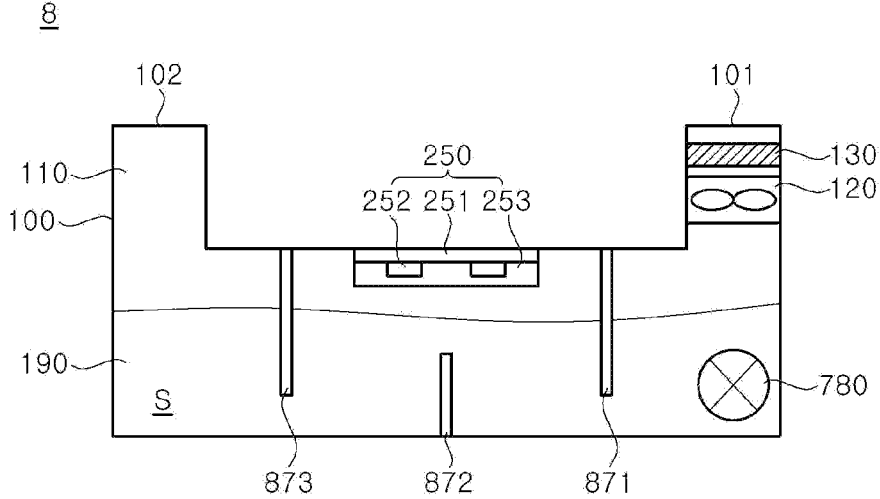
871 ⎫
872 ⎬ 870
873 ⎭
【FIG. 10】
<u>9</u>
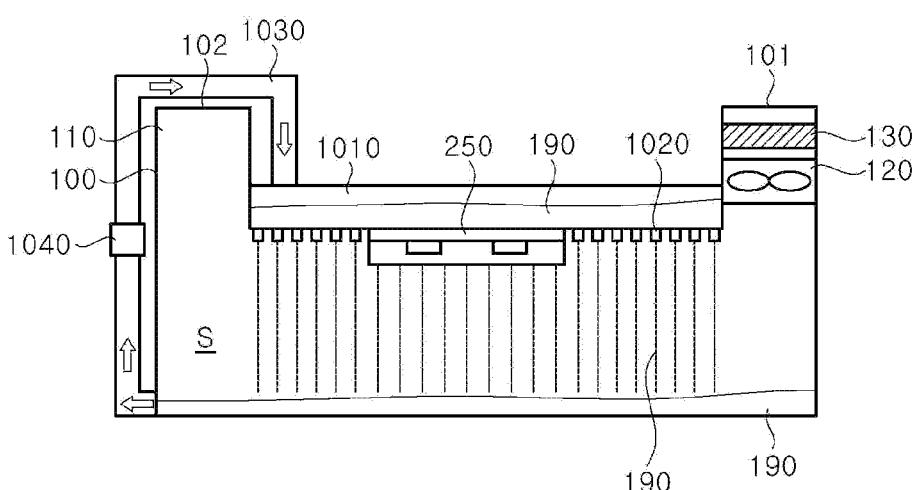

【FIG. 11】
<u>10</u>
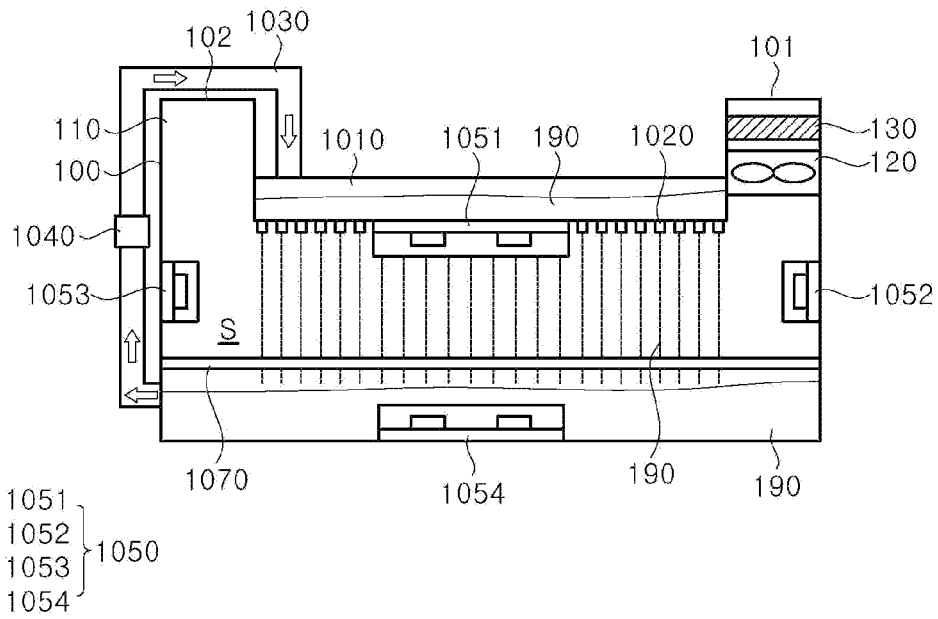
$$\left.\begin{matrix} 1051 \\ 1052 \\ 1053 \\ 1054 \end{matrix}\right\} 1050$$
【FIG. 12】
<u>11</u>
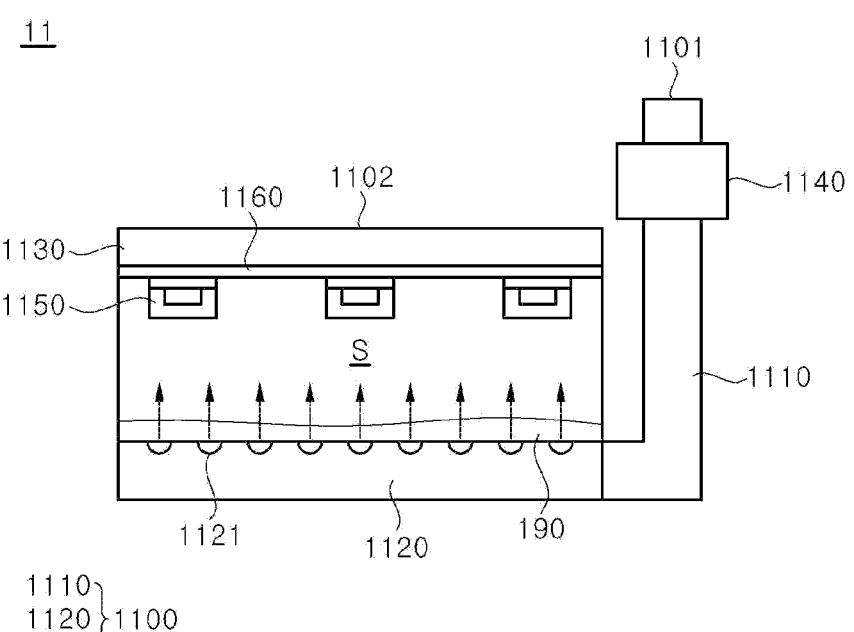
$$\left.\begin{matrix} 1110 \\ 1120 \\ 1130 \end{matrix}\right\} 1100$$

【FIG. 13】
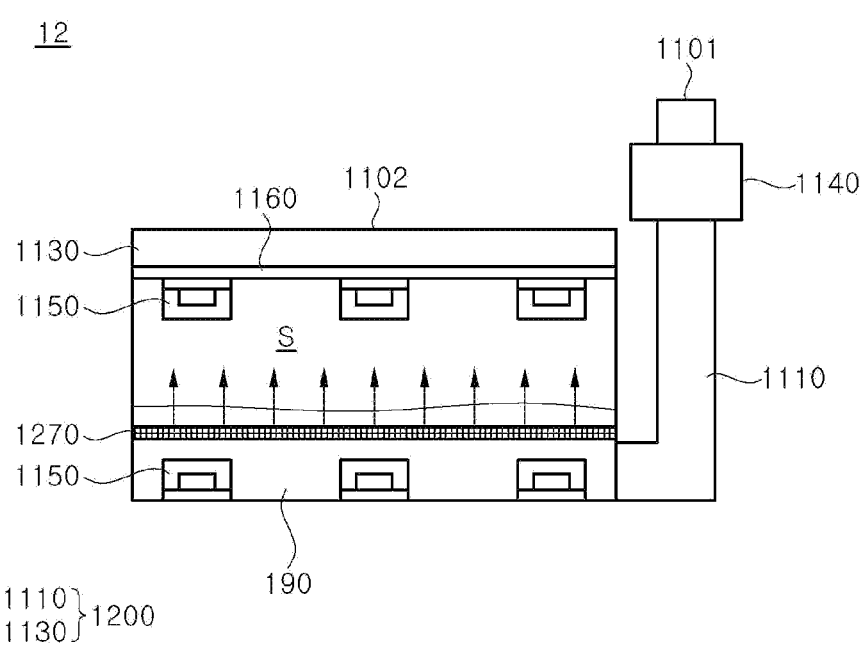
【FIG. 14】
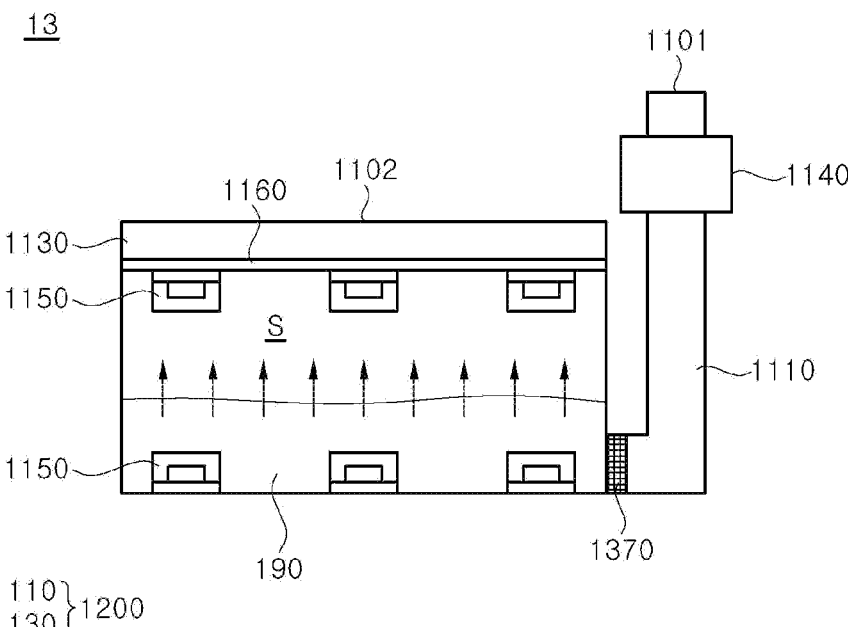

【FIG. 15】
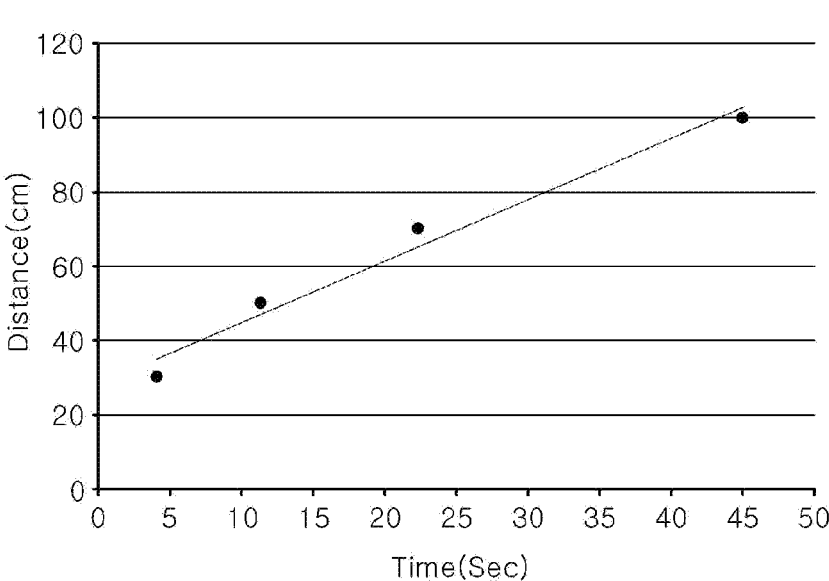
【FIG. 16】
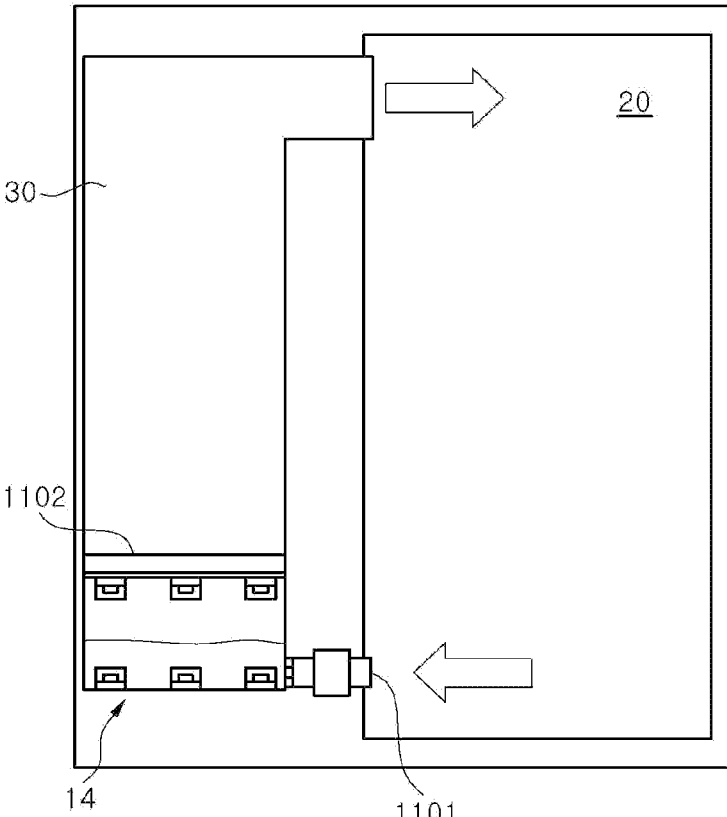

FLUID TREATMENT APPARATUS

CROSS REFERENCE TO RELATED APPLICATIONS

This application is a National Stage Entry of International Application No. PCT/KR2021/012718, filed on Sep. 16, 2021, which claims priority from and the benefit of U.S. Provisional Application No. 63/079,076, filed on Sep. 16, 2020, each of which is incorporated by reference for all purposes as if fully set forth herein.

BACKGROUND

Field

Exemplary embodiments of the invention relate generally to a fluid treatment device.

DISCUSSION OF THE BACKGROUND

In recent years, as environmental pollution due to industrialization and large-scale infectious diseases has increased, interests in personal and public hygiene have also increased. Accordingly, as demand for sterilized water or purified air is increasing, sterilization-related products capable of creating a safe environment free from pathogenic microorganisms are being developed.

In a typical air purifier, the capacity may need to be changed according to a purification amount of air or a purification target area, which creates a problem in that the size of the air purifier needs to be increased with increasing capacity thereof.

The above information disclosed in this Background section is only for understanding of the background of the inventive concepts, and, therefore, it may contain information that does not constitute prior art.

SUMMARY

Exemplary embodiments provide a fluid treatment device capable of improving sterilization efficiency.

Exemplary embodiments also provide a fluid treatment device capable of improving sterilization efficiency by exposing contaminants contained in fluid to light having sterilization properties for a sufficient amount of time.

Additional features of the inventive concepts will be set forth in the description which follows, and in part will be apparent from the description, or may be learned by practice of the inventive concepts.

In accordance with one aspect of the present disclosure, there is provided a fluid treatment device including: a pipe having an inlet through which fluid is introduced into the pipe from a fluid treatment space, an outlet through which sterilized fluid is discharged to the fluid treatment space, and a flow channel connecting the inlet to the outlet, the pipe providing a sterilization area in the flow channel; a solvent filling at least a portion of the sterilization area; and at least one light source module disposed in the sterilization area, the light source module including a light source emitting sterilizing light and a substrate on which the light source is mounted.

The fluid introduced through the inlet may pass through the solvent towards the outlet, the solvent may trap contaminants contained in the fluid when the fluid passes through the solvent, and the light source module may sterilize the solvent with the contaminants trapped therein.

The light source module may be disposed in at least one of a region inside the solvent and a region above the solvent.

The light source module may sterilize at least one of the fluid passing through the solvent and the fluid having passed through the solvent.

The fluid treatment device may further include: an inflow guide formed on an inner wall of the pipe and having one end placed inside the solvent, the inflow guide guiding the fluid introduced through the inlet to flow into the solvent.

The fluid treatment device may further include: at least one guide disposed in the sterilization area and having at least a portion placed inside the solvent, the guide increasing a length of a flow path of the fluid.

The fluid treatment device may further include: a filter placed inside the solvent and trapping or sterilizing contaminants contained in the solvent and contaminants and in the fluid passing through the solvent.

The light source module may sterilize the contaminants trapped in the filter.

The fluid treatment device may further include: a circulation member forcing the solvent to flow.

The fluid treatment device may further include: a solvent storage storing the solvent; a solvent discharge portion discharging the solvent from the solvent storage to the sterilization area; and a solvent channel through which the solvent discharged to the sterilization area moves to the solvent storage.

The solvent discharge portion may discharge the solvent to the sterilization area in the form of a thin stream or a fine spray.

The fluid treatment device may further include: a filter disposed between a bottom of the sterilization area and the solvent discharge portion. The filter may trap or sterilize contaminants contained in the solvent and in the fluid passing through the solvent.

The light source module may sterilize the contaminants trapped in the filter.

The fluid treatment device may further include: a fluid discharge portion through which the fluid introduced through the inlet is discharged into the solvent. The solvent discharge portion may split the fluid into multiple streams before the fluid is discharged into the solvent.

The fluid may be introduced from a lower region of the fluid treatment space.

The sterilized fluid may be discharged to an upper region of the fluid treatment space.

The fluid treatment device may further include: at least one of a fan and a fluid pump to force the fluid to flow from the fluid treatment space into the inlet.

The fluid treatment device may further include: a filter filtering the contaminants contained in the fluid before the fluid is introduced into the sterilization area.

The light source module may further include a protective member covering the substrate and the light source. The protective member protects the substrate and the light source from the solvent and may be formed of a light transmitting material.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

FIG. 1 is a view of a fluid treatment apparatus according to a first exemplary embodiment.

FIG. 2 is a view of a fluid treatment apparatus according to a second exemplary embodiment.

FIG. 3 is a view of a fluid treatment apparatus according to a third exemplary embodiment.

FIG. 4 is a view of a fluid treatment apparatus according to a fourth exemplary embodiment.

FIG. 5 is a view of a fluid treatment apparatus according to a fifth exemplary embodiment.

FIG. 6 is a sectional view taken in one direction of a fluid treatment device according to a sixth exemplary embodiment.

FIG. 7 is a sectional view taken in another direction of the fluid treatment device according to the sixth exemplary embodiment.

FIG. 8 is a view of a fluid treatment apparatus according to a seventh exemplary embodiment.

FIG. 9 is a view of a fluid treatment apparatus according to an eighth exemplary embodiment.

FIG. 10 is a view of a fluid treatment apparatus according to a ninth exemplary embodiment.

FIG. 11 is a view of a fluid treatment apparatus according to a tenth exemplary embodiment.

FIG. 12 is a view of a fluid treatment apparatus according to an eleventh exemplary embodiment.

FIG. 13 is a view of a fluid treatment apparatus according to a twelfth exemplary embodiment.

FIG. 14 is a view of a fluid treatment apparatus according to a thirteenth exemplary embodiment.

FIG. 15 is a graph depicting sterilization efficiency of a light source module included in a fluid treatment apparatus according to an exemplary embodiment.

FIG. 16 is a view of a fluid treatment apparatus according to an exemplary embodiment provided to a fluid treatment space.

DETAILED DESCRIPTION

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z- axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 is a view of a fluid treatment device according to a first exemplary embodiment.

A fluid treatment device 1 according to the first exemplary embodiment may include a pipe 100, a fan 120, a first filter 130, a first light source module 150, and a second light source module 160.

Referring to FIG. 1, the pipe 100 is formed with a flow channel 110 defining a path through which fluid introduced into the pipe flows. In addition, the pipe 100 may include an inlet 101 corresponding to a path through which the fluid flows into the flow channel 110 from an outside of the pipe 100, and an outlet 102 corresponding to a path through which the fluid is discharged from the flow channel 110 to the outside of the pipe 100. In addition, the pipe 100 may provide a sterilization area S, which is an area or space where sterilization of fluid containing contaminants is performed. Here, the term 'sterilizing' the fluid and/or a solvent means removing or sterilizing contaminants contained in the fluid and/or the solvent.

The sterilization area S is filled with a solvent 190. The solvent 190 may be a liquid or gas capable of separating contaminants from the fluid. For example, the solvent 190 may be water or a liquid including a component capable of removing the contaminants. In addition, the solvent 190 may be one of an inorganic solvent, an organic solvent, a polar solvent, and a non-polar solvent. For example, the inorganic solvent may be water, and the organic solvent may be ether, acetone, or alcohol. The polar solvent may be one of water, ethanol, and acetone. In addition, the non-polar solvent may include cyclohexane carbon tetrachloride, benzene, and the like.

In addition, according to this exemplary embodiment, the temperature, pH, ionic constant, and dielectric constant of the solvent 190 may be adjusted to increase solubility of contaminants in the solvent 190.

In addition, the solvent 190 may include a substance capable of sterilizing at least some of the contaminants.

Referring to FIG. 1, the inlet 101 and the outlet 102 are placed above the sterilization area S.

An inner wall of the pipe 100 may include a material that reflects light. For example, a light reflective material may be coated on the inner wall of the pipe 100. Alternatively, the pipe 100 may be formed of a light reflective material or a material including a light reflective material. In addition, the entire inner wall of the pipe 100 may include a light reflective material. Alternatively, the light reflective material may be present only on the inner wall defining the sterilization area S, in which sterilization of the fluid is performed.

The first light source module 150 and the second light source module 160 may be disposed in the flow channel 110 of the pipe 100.

The first light source module 150 and the second light source module 160 may be disposed on the inner wall of the pipe 100 to emit light for sterilization of contaminants. The first light source module 150 and the second light source module 160 emit light having a wavelength capable of sterilizing contaminants trapped in the sterilization area S. For example, the light may be UV light. However, the inventive concepts are not limited thereto, and the kind of sterilizing light may be changed according to the kind of fluid and the sterilization purpose.

In addition, each of the first light source module 150 and the second light source module 160 may include at least one light source 152, 162 that generates and emits light and a substrate 151, 161 on which the light source 152, 162 is mounted. The first light source module 150 and the second light source module 160 may emit different kinds of light. Alternatively, each of the first light source module 150 and the second light source module 160 may include multiple light sources 152, 162, which emit the same or different kinds of light.

In addition, the first light source module 150 and the second light source module 160 may be placed inside the solvent 190. Here, each of the first light source module 150 and the second light source module 160 may include a protective member 153, 163 to prevent damage thereto due to contact with the solvent 190. The protective member 153, 163 may diffuse light emitted from the light source 152, 162, in addition to providing waterproofness.

The protective member 153, 163 may be formed of a material that transmits light from the light source 152, 162 therethrough. For example, the protective member 153, 163 may be formed of glass, quartz, sapphire, or the like. However, the inventive concepts are not limited thereto, and the protective member 153, 163 may be formed of any material capable of both light transmission and waterproofing, other than the glass, quartz, or sapphire.

According to this exemplary embodiment, the first light source module 150 and the second light source module 160 may face each other at opposite ends of the sterilization area S. That is, both the first light source module 150 and the second light source module 160 may emit light for sterilization in a longitudinal direction of the sterilization area S.

Accordingly, the first light source module 150 may emit light in the same direction as a flow direction of the fluid. In addition, the second light source module 160 may emit light in a direction opposite to the flow direction of the fluid.

According to this exemplary embodiment, the fluid introduced through the inlet 101 may flow into the sterilization area S along the flow channel 110. The fluid introduced into the sterilization area S passes through the solvent 190 filling the sterilization area S towards the outlet 102.

When the fluid passes through the sterilization area S, the solvent 190 separates contaminants from the fluid through adsorption of the contaminants thereto. Thus, the contaminants separated from the fluid may be trapped in the solvent 190.

The fluid may be decontaminated and purified while passing through the sterilization area S. The purified fluid may be discharged from the fluid treatment device 1 through the outlet 102.

In addition, the first light source module 150 and the second light source module 160 may sterilize contaminants trapped in the solvent 190 by irradiating the sterilization area S with light. That is, the first light source module 150 and the second light source module 160 may sterilize the solvent 190 containing contaminants by irradiating the solvent 190 with light.

When the solvent 190 includes a substance capable of sterilizing contaminants, the solvent 190 may also sterilize contaminants trapped therein.

According to this exemplary embodiment, the pipe 100 may have a structure in which a length of the flow channel 110 is greater than a diameter of the flow channel 110.

In the fluid treatment device 1 according to this exemplary embodiment, the sterilization area S can be maximized by the structure, in which the flow channel 110 of the pipe 100 extends to have a long length in the longitudinal direction, and the first light source module 150 and the second light source module 160 are disposed at opposite ends of the flow channel 110, respectively.

In the fluid treatment device 1 according to this exemplary embodiment, the amount of the fluid that can be simultaneously sterilized is increased due to the structure that maximizes the sterilization area S, thereby improving sterilization efficiency with respect to the fluid. In addition, in the fluid treatment device 1 according to this exemplary embodiment, since the sterilization area S has a long length, it is possible to increase a residence time of the fluid in the sterilization area S while passing therethrough, thereby improving sterilization efficiency with respect to the fluid.

That is, the fluid treatment device 1 according to this exemplary embodiment can maximize the amount of contaminants trapped in the solvent 190 by increasing the amount of the fluid passing through the sterilization area S, and increasing the residence time of the fluid in the sterilization area S while passing therethrough.

In addition, since contaminants trapped in the solvent 190 stored inside the pipe cannot escape from the sterilization area S, it is possible to increase an exposure time of the contaminants to light.

Accordingly, the fluid treatment device 1 according to this exemplary embodiment can improve sterilization efficiency by allowing as many contaminants as possible to be trapped in the solvent, and sterilizing the contaminants through irradiation with light for a sufficient amount of time.

The fan 120 may be disposed inside and/or outside the pipe 100. In addition, the fan 120 may be disposed near at least one of the inlet 101 and the outlet 102. In FIG. 1, the fan 120 is illustrated as being placed near the inlet 101 inside the pipe 100. However, the inventive concepts are not limited thereto, and the arrangement and the number of fans may be changed in various ways so long as the fan 120 can generate flow of the fluid, such that the fluid passes through the sterilization area S inside the pipe 100.

In addition, the fan 120 may control a flow rate of the fluid. The fluid treatment device 1 according to this exemplary embodiment may control the flow rate of the fluid by changing a rotation speed of the fan 120, the number of fans 120 operated, and the like.

The fluid treatment device 1 according to this exemplary embodiment can improve sterilization efficiency by controlling the flow rate of the fluid passing through the sterilization area S using the fan 120.

As such, the fluid treatment device 1 according to this exemplary embodiment may control the amount and flow rate of the fluid passing through the sterilization area S by adjusting the fan 120 and the length of the sterilization area S. Accordingly, the fluid treatment device 1 according to this exemplary embodiment can improve sterilization efficiency with respect to the fluid by sufficiently irradiating the fluid passing through the pipe 100 with light, such that contaminants in the fluid sufficiently react with the light.

Although the flow of fluid is controlled using the fan 120 in this exemplary embodiment, the inventive concepts are not limited thereto. For example, instead of the fan 120, a fluid pump, such as an air pump, may be connected to the inlet 101 to force fluid to flow from the outside of the fluid treatment device 1 into the inlet 101. In addition, apart from the fluid pump, any device capable of forcing fluid to flow into and through the fluid treatment device 1 may be used in the fluid treatment device 1 instead of the fan 120.

The fluid treatment device 1 according to this exemplary embodiment may further include at least one first filter 130.

Referring to FIG. 1, the first filter 130 may be disposed between the fan 120 and the inlet 101. In this structure, some contaminants contained in the fluid may be filtered out by the first filter 130. Accordingly, with the first filter 130, the fluid treatment device 1 according to this exemplary embodiment can minimize contamination of the fan 120 from the contaminants in the fluid.

Although the first filter 130 is illustrated as being disposed between the fan 120 and the inlet 101 in FIG. 1, however, the inventive concepts are not limited thereto. In other exemplary embodiments, the filter 130 may be provided to at least one of a front end and a rear end of the fan 120. In addition, for the fluid treatment device including multiple first filters 130, the first filters 130 may be different types of first filters 130.

In addition, the first filter 130 may include multiple layers of different materials. For example, the first filter 130 may include a first filter layer 131 and a second filter layer 132.

The first filter layer 131 may have multiple orifices having a smaller size than contaminants in the fluid. Accordingly, the first filter layer 131 may filter out the contaminants while allowing the fluid to pass therethrough.

The second filter layer 132 may be formed of a different material than the first filter layer 131. The second filter layer 132 may be formed of a material having better rigidity or hardness than the first filter layer 131.

The second filter layer 132 may be formed on at least one of the front end and the rear end of the first filter layer 131 to prevent the first filter layer 131 from being damaged by the fluid flowing at a fast speed.

The concentration of contaminants in the fluid passing through the sterilization area S can be reduced by the first filter 130.

Since the concentration of contaminants to be sterilized by light is reduced by the first filter 130, the fluid treatment device 1 according to this exemplary embodiment can improve sterilization efficiency with respect to the fluid given the same exposure time and the same quantity of light.

Next, a fluid treatment device according to other exemplary embodiments will be described. Here, the following description will focus on different features of the fluid treatment device with respect to the fluid treatment device 1 according to the first exemplary embodiment. For details of omitted or briefly described features, refer to the above description.

FIG. 2 is a view of a fluid treatment device according to a second exemplary embodiment.

According to the second exemplary embodiment, the fluid treatment device 2 may include a pipe 100, a fan 120, a first filter 130, and a light source module 250. The light source module 250 may include a substrate 251 and multiple light sources 252 mounted on the substrate 251. In addition, the light source module 250 may further include a protective member 253 covering the substrate 251 and the multiple light sources 252 to protect the substrate 251 and the multiple light sources 252 from a solvent.

Referring to FIG. 2, in the fluid treatment device 2 according to the second exemplary embodiment, the light source module 250 is placed in the sterilization area S. In addition, the light source module 250 may be mounted on the pipe 100, such that a lower surface of the substrate 251 faces an inner wall of the pipe 100. Here, the lower surface of the substrate 251 is an opposite surface to the surface of the substrate on which the light sources 252 are mounted. That is, the light sources 252 are mounted on an upper surface of the substrate 251.

In this exemplary embodiment, the light source module 250 is placed at an upper portion of the sterilization area S. Alternatively, the light source module 250 may be placed at each of the upper and lower portions of the sterilization area S.

According to this exemplary embodiment, since the light source module 250 is placed above the flow channel 110, a distance between the light source module 250 and the fluid is shorter than in the above exemplary embodiment. That is, a light irradiation distance of the light source module 250 can be reduced. A shorter light irradiation distance provides higher light intensity.

That is, the fluid treatment device 2 according to this exemplary embodiment can increase the intensity of light emitted to the fluid by reducing the distance between the light source module 250 and the fluid.

Accordingly, the fluid treatment device 2 according to this exemplary embodiment can improve sterilization efficiency with respect to the fluid by increasing the intensity of light emitted to the fluid.

The fluid containing contaminants may be introduced into the sterilization area S through an inlet 101. In the fluid treatment device 2 according to this exemplary embodiment, a solvent 190 may fill a portion of the sterilization area S, unlike in the fluid treatment device 1 show in FIG. 1. Accordingly, the sterilization area S may be divided into a region filled with the solvent 190 and a solvent-free region. For example, the solvent 190 may fill the sterilization area S to a level that can prevent the fluid introduced into the sterilization area S from contacting the light source module 250.

Some portion of the fluid introduced into the sterilization area S passes through the solvent 190 towards an outlet 102. Accordingly, the portion of the fluid may be decontaminated and purified by the solvent 190. Here, contaminants trapped in the solvent 190 may be sterilized by light emitted from the light source module 250 to the solvent 190.

The other portion of the fluid may pass through a space between the light source module 250 and the solvent 190 towards the outlet 102. That is, the portion of the fluid, which does not pass through the solvent 109, passes through a region irradiated with light emitted from the light source module 250. Accordingly, the portion of the fluid, which does not pass through the solvent 109, can also be sterilized through exposure to light from the light source module 250.

As such, in the fluid treatment device 2 according to this exemplary embodiment, the light source module 250 may be placed above the solvent 190 to be spaced apart from the solvent 190. In this structure, since the light source module 250 is spaced apart from the solvent 190, it is possible to prevent the light source module 250 from being damaged by the solvent 190. In this case, the protective member 253 may be omitted from the light source module 250.

The fluid treatment device 2 according to this exemplary embodiment may include multiple light source modules 250. In the fluid treatment device 2 according to this exemplary embodiment, the multiple light source modules 250 may be arranged along the pipe 100, thereby further improving sterilization efficiency with respect to the fluid.

FIG. 3 is a view of a fluid treatment device according to a third exemplary embodiment.

The fluid treatment device 3 according to the third exemplary embodiment has a structure in which an inflow guide 370 is added to the fluid treatment device 2 shown in FIG. 2.

The inflow guide 370 may guide movement of fluid from the flow channel 110 connected to the inlet 101 into the solvent 190 in the sterilization area S. That is, the inflow guide 370 defines a flow path of the fluid from an entrance of the sterilization area S to the solvent 190 in the sterilization area S.

For example, the inflow guide 370 may downwardly extend from an upper surface of the pipe 110 near the entrance of the sterilization area S, as shown in FIG. 3.

Here, the inflow guide 370 may be formed such that a lower end thereof is immersed in the solvent 190 while being spaced apart from a bottom surface of the sterilization area S.

When the fluid enters the sterilization area S, the fluid is introduced into the solvent 190 along the inflow guide 370.

With the inflow guide 370 guiding movement of the fluid from the inlet 101 into the solvent 190 in the sterilization area S, the fluid treatment device 3 according to this exemplary embodiment allows the entirety of the fluid to pass through the solvent 190 and to be purified by the solvent 190.

Although the inflow guide 370 is illustrated as a separate component from the inlet 101 in this exemplary embodiment, the inventive concepts are not limited thereto, and the inflow guide 370 may be integrally formed with an inner wall of the pipe defining the inlet 101 in other exemplary embodiments. That is, in the fluid treatment device 3 according to this exemplary embodiment, the inner wall of the pipe 110 defining the inlet 101 and the flow channel 110 connected to the inlet 101 may be formed long enough to be immersed in the solvent 190.

FIG. 4 is a view of a fluid treatment device according to a fourth exemplary embodiment.

The fluid treatment device 4 according to the fourth exemplary embodiment has a structure in which a light source module 250 is added to the fluid treatment device 3 shown in FIG. 3.

According to this exemplary embodiment, the fluid treatment device 4 may include multiple light source modules 250 disposed at different locations. For example, the multiple light source modules 250 may include a first light source module 255 and a second light source module 256.

Referring to FIG. 4, the first light source module 255 may be disposed on an upper inner wall of the pipe 100 defining the sterilization area S. That is, the first light source module 255 is placed above the solvent 190, like the light source module 250 shown in FIG. 3. In addition, the first light source module 255 may include a protective member 253, which may be omitted as necessary. The first light source module 255 emits light for sterilization toward the solvent 190 from above the solvent 190.

In addition, the second light source module 256 may be disposed on a lower inner wall of the pipe 100 defining the sterilization area S. Accordingly, the second light source module 256 is disposed in the solvent 190 to emit light for sterilization from inside the solvent 190.

At least a portion of light emitted from the first light source module 255 may be reflected from an interface between the atmosphere and the solvent 190 into the atmosphere due to a difference in index of refraction between the atmosphere and the solvent 190. Accordingly, the quantity of light entering the solvent 190 can be reduced, causing contaminants trapped in the solvent 190 to be insufficiently exposed to light.

According to this exemplary embodiment, since the second light source module 256 is disposed inside the solvent 190, it is possible to prevent the contaminants from being insufficiently exposed to light.

That is, the fluid treatment device 4 according to this exemplary embodiment can irradiate the solvent with light from both outside and inside of the solvent 190 by further disposing the light source module 250 inside the solvent 190. Accordingly, the fluid treatment device 4 according to this exemplary embodiment can improve sterilization efficiency by allowing contaminants trapped in the solvent 190 to be exposed to more light.

FIG. 5 is a view of a fluid treatment device according to a fifth exemplary embodiment.

The fluid treatment device 5 according to the fifth exemplary embodiment may include a pipe 100, a fan 120, a first filter 130, a guide 570, and a light source module 250.

The fluid treatment device 5 according to the fifth exemplary embodiment has a structure in which at least one guide 570 is added to the fluid treatment device 2 shown in FIG. 2.

Referring to FIG. 5, the guide 570 may be disposed in the sterilization area S. The guide 570 extends from an upper inner wall of the pipe 100 toward a bottom surface of the sterilization area S. Here, an end of the guide 570 is placed in the solvent 190 and is spaced apart from the bottom surface of the sterilization area S. Here, the bottom surface of the sterilization area S corresponds to a lower inner wall of the pipe 100 (see FIG. 5).

Accordingly, the fluid passes through a lower space defined between the inner wall of the pipe 100 and the guide 570 while passing through the sterilization area S.

Here, the guide 570 hinders movement of the fluid introduced into the sterilization area S into the atmosphere, thereby allowing the entirety of the fluid to move to the solvent 190. In addition, some portion of the fluid may also collide with a portion of the guide 570 placed in the solvent 190 while passing through the solvent 190.

In addition, the solvent 190 is also moved by movement of the fluid passing through the solvent 190 and thus some portion of the solvent 190 also collides with the guide 570.

As the fluid and the solvent 190 collide with the guide 570, a vortex may be generated in the solvent 190.

The vortex can increase the residence time of the fluid in the solvent 190.

In addition, the vortex can reduce the speed at which the fluid moves by interfering with movement of the fluid.

In addition, the guide 570 can increase a length of a flow path of the fluid through the sterilization area S.

In this way, it is possible to increase the residence time of the fluid in the solvent 190 while further facilitating separation of contaminants from the fluid through generation of the vortex.

Accordingly, the fluid treatment device 5 according to this exemplary embodiment can secure sufficient force and time to separate contaminants from the fluid, thereby improving purification efficiency with respect to the fluid.

In addition, the fluid treatment device 5 according to this exemplary embodiment can improve sterilization efficiency by allowing as many contaminants as possible to be trapped in the solvent 190 and sterilizing the solvent 190 with the contaminants trapped therein.

According to this exemplary embodiment, the guide 470 may be formed of a light reflective material. The guide 470 formed of the light reflective material reflects light emitted to sterilize contaminants such that the solvent 190 and the sterilization area S can be uniformly irradiated with the light. As such, the guide 470 serves to minimize a region of the sterilization area S not irradiated with light, thereby improving sterilization efficiency of the fluid treatment device 5.

FIG. 6 and FIG. 7 are views of a fluid treatment device according to a sixth exemplary embodiment.

FIG. 6 is a sectional view taken in one direction of the fluid treatment device according to the sixth exemplary embodiment, and FIG. 7 is a sectional view taken in another direction of the fluid treatment device according to the sixth exemplary embodiment.

The fluid treatment device 6 according to the sixth exemplary embodiment may include a pipe 100, a fan 120, a first filter 130, a second filter 670, and a light source module 250.

The fluid treatment device 6 according to the sixth exemplary embodiment has a structure in which at least one second filter 670 is added to the fluid treatment device 2 shown in FIG. 2.

Referring to FIG. 6, the second filter 670 may be disposed in the sterilization area S. The second filter 670 upwardly extends from a lower inner wall of the pipe 100. That is, the second filter 670 may be disposed inside the solvent 190.

The second filter 670 may be formed of a material capable of adsorbing contaminants contained in fluid. Thus, the second filter 670 may adsorb contaminants trapped in the solvent 190 while the fluid passes through the second filter 670. The contaminants adsorbed to the second filter 670 may be sterilized through exposure to light from the light source module 250 for a sufficient time. Accordingly, the fluid treatment device 6 according to this exemplary embodiment can improve sterilization efficiency through the second filter 670.

Alternatively, the second filter 670 may be formed of a material that can adsorb or remove contaminants through reaction with the solvent 190 or light emitted from the light source module 250.

For example, the second filter 250 may be a filter capable of trapping or removing contaminants, such as a trap filter or a photocatalytic filter.

With the second filter 670 capable of removing contaminants through reaction with the solvent 190, the fluid treatment device according to this exemplary embodiment can further improve sterilization efficiency through combination of sterilization of contaminants using light from the light source module and sterilization of contaminants using the filters and the solvent.

For example, the second filter 670 may be formed to block a portion of the flow channel defining the sterilization area S.

Referring to FIG. 7, the second filter 670 may be formed such that both side surfaces and a lower surface thereof closely contact an inner wall of the pipe 100. In addition, the second filter 670 may include multiple through-holes 671 allowing passage of the solvent 190 and the fluid therethrough. That is, the second filter 670 may include multiple through-holes 671 opened in the same direction as a flow direction of the fluid.

Accordingly, the fluid may pass through the through-holes 671 of the second filter 670 while passing through the solvent 190. When the fluid passes though the through-holes 671, contaminants contained in the fluid or contaminants trapped in the solvent 190 may be adsorbed to the second filter 670.

In addition, according to this exemplary embodiment, the second filter 670 may generate a vortex through collision with the solvent 190 and the fluid passing through the solvent 190. That is, the second filter 670 may perform the same function as the guide 570 of the fluid treatment device 5 shown in FIG. 5.

Accordingly, the fluid treatment device according to this exemplary embodiment can improve sterilization efficiency through the second filter 670 configured to generate a vortex in the fluid and the solvent 190 and to reduce the flow rate of the fluid.

Although the second filter 670 is illustrated as having the multiple through-holes 671 in this exemplary embodiment, the inventive concepts are not limited thereto. For example, the second filter 670 may be composed of multiple columns spaced apart from one another in some exemplary embodiments. Alternatively, the second filter 670 may be composed of multiple structures floating in and on the solvent 190. Still alternatively, the through holes 671 of the second filter 670 may have a smaller size than contaminants in the fluid. As such, the second filter 670 may be any structure that can adsorb or remove contaminants contained in the fluid and contaminants trapped in the solvent 190 at a location inside or outside the solvent 190.

FIG. 8 is a view of a fluid treatment device according to a seventh exemplary embodiment.

The fluid treatment device 7 according to the seventh exemplary embodiment may include a pipe 100, a fan 120, a first filter 130, a circulation member 780, and a light source module 250.

The fluid treatment device 7 according to the seventh exemplary embodiment has a structure in which the circulation member 780 is added to the fluid treatment device 2 shown in FIG. 2.

The circulation member 780 circulates the solvent 190 through the sterilization area S. For example, the circulation member 780 may be any device that can force the solvent 170 to flow, for example, a fan.

According to this exemplary embodiment, contaminants can be more easily separated from the fluid passing through the solvent 190 by force of the solvent 190 circulating through the sterilization area S by means of the circulation member 780. Accordingly, contaminants can be more efficiently trapped in the solvent 190 circulating through the sterilization area S, whereby purification of the fluid can be performed more efficiently.

In addition, according to the present exemplary embodiment, as the solvent 190 is circulated by the circulation member 780, contaminants trapped in the solvent 190 are also moved. As such, contaminants trapped in a region unreachable by light from the light source module 250 can also be exposed to the light from the light source module 250 while being moved along with the solvent 190.

Accordingly, the fluid treatment device 7 according to this exemplary embodiment can improve sterilization efficiency through the circulation member 780 configured to allow all contaminants trapped in the solvent 190 to be completely exposed to light from the light source module 250.

FIG. 9 is a view of a fluid treatment device according to an eighth exemplary embodiment.

The fluid treatment device 8 according to the eighth exemplary embodiment may include a pipe 100, a fan 120, a first filter 130, a guide 870, a circulation member 780, and a light source module 250.

The fluid treatment device 8 according to the eighth exemplary embodiment has a structure in which the guide 870 is added to the fluid treatment device 7 shown in FIG. 8.

The guide 870 of the fluid treatment device 8 according to the eighth exemplary embodiment has the same function as the guide 570 of the fluid treatment device 5 shown in FIG. 5.

Referring to FIG. 8, the guide 870 may include a first guide 871, a second guide 872, and a third guide 873. Here, the first guide 871 and the third guide 873 may be formed on a lower inner wall of the pipe 100, and the second guide 871 may be formed on an upper inner wall of the pipe 100. Accordingly, the fluid sequentially passes through a region inside the solvent 190 below the first guide 871, a region inside the solvent 190 above the second guide 872, and a region inside the solvent 190 below the third guide 873 while moving towards the outlet 102. In this way, the multiple guides 870 can increase a flow path of the fluid.

The circulation member 780 of the fluid treatment device 8 according to this exemplary embodiment may force the solvent 190, through which the fluid passes, to flow. Accordingly, the fluid treatment device 8 can improve contaminant trapping efficiency of the solvent by the force of flow of the solvent 190. In addition, the fluid treatment device 8 allows contaminants trapped in the solvent 190 to also be moved along with the solvent 190 circulating through the sterilization area S, thereby ensuring exposure of all contaminants trapped in the solvent 190 to light from the light source module 250.

In addition, with the guide 870, the fluid treatment device 8 according to this exemplary embodiment may generate a vortex in the solvent 190 and the fluid to reduce the flow rate of the fluid. Further, the fluid treatment device 8 according to this exemplary embodiment can increase a length of the flow path of the fluid in the sterilization area S through arrangement of the multiple guides 870. Accordingly, the fluid treatment device 8 can increase a residence time of the fluid in the solvent 190, such that the solvent 190 can sufficiently trap contaminants, thereby improving purification efficiency with respect to the fluid.

As such, through combination of the circulation member 780 and the guide 870, the fluid treatment device 8 according to this exemplary embodiment can secure sufficient time for the solvent 190 to trap contaminants, thereby ensuring sufficient purification of fluid, and can allow all contaminants trapped in the solvent 190 to be sufficiently exposed to light, thereby ensuring sufficient sterilization of contaminants.

Although the fluid treatment device 9 according to this exemplary embodiment is illustrated as including multiple guides 870, the inventive concepts are not limited thereto, and multiple second filters 670 shown in FIG. 6 may be arranged like the multiple guides 870. In this arrangement, since contaminants are adsorbed to the multiple second filters 670 as shown in FIG. 6, fluid purification efficiency and contaminant sterilization efficiency of the fluid treatment device can be further improved.

FIG. 10 is a of a fluid treatment device according to a ninth exemplary embodiment.

The fluid treatment device 9 according to the ninth exemplary embodiment includes a pipe 100, a fan 120, a first filter 130, a light source module 250, a solvent storage 1010, a solvent channel 1030, and a circulation pump 1040.

The solvent storage 1010 may be placed on an upper side of the pipe 100. Referring to FIG. 10, the solvent storage 1010 is placed above the sterilization area S.

The solvent storage 1010 stores the solvent 190. In addition, the solvent storage 1010 may be connected to a solvent discharge portion 1020 disposed in the sterilization area S.

The solvent 190 stored in the solvent storage 1010 may be discharged to the sterilization area S through the solvent discharge portion 1020. Here, the solvent discharge portion 1020 may discharge the solvent 190 in the form of a thin stream. Alternatively, the solvent discharge portion 1020 may discharge the solvent 190 in the form of a fine spray.

Referring to FIG. 10, the solvent discharge portion 1020 may be disposed at an upper portion of the sterilization area S. Accordingly, the solvent 190 falls downwards from the upper portion of the sterilization area S. In FIG. 10, the solvent discharge portion 1020 is illustrated as multiple nozzles. However, the inventive concepts are not limited thereto, and the solvent discharge portion 1020 may be any structure that can discharge the solvent 190 from the solvent storage 1010 to the sterilization area S in the form of a thin stream or a fine spray.

According to this exemplary embodiment, the fluid introduced through the inlet 101 passes through the solvent 190 falling from the upper portion of the sterilization area S. Here, the solvent 190 contacting the fluid traps contaminants contained in the fluid before falling to the bottom of the sterilization area S. In addition, the fluid, thus decontaminated and purified, passes through the sterilization area S toward the outlet 102.

In addition, according to this exemplary embodiment, the fluid may be exposed to light from the light source module 250 while passing through the sterilization area S. Accordingly, even the fluid that fails to be purified by the falling solvent 190 can also be sterilized by light from the light source module 250.

The solvent 190 discharged from the solvent discharge portion 1020 is collected on the bottom of the sterilization area S. The solvent 190 collected in the sterilization area S is in a state of trapping contaminants separated from the fluid. The solvent 190 with the contaminants trapped therein can be sterilized through exposure to light from the light source module 250 while staying in the sterilization area S. That is, the solvent 190 can be sterilized by light both while falling from the upper portion of the sterilization area S and while staying at the bottom of the sterilization area S. Accordingly, the fluid treatment device 9 according to this exemplary embodiment can improve sterilization efficiency.

Referring to FIG. 10, the sterilization area S may be connected to the solvent channel 1030. The solvent channel 1030 connects the sterilization area S to the solvent storage 1010.

The circulation pump 1030 may force the solvent 190 at the bottom of the sterilization area S to move to the solvent storage 1010 through the solvent channel 1030.

Since the solvent 190 collected at the bottom of the sterilization area S is sterilized by light from the light source module 250, the solvent 190 stored in the solvent storage 1010 is in a sterilized state.

In addition, the fluid treatment device 9 according to this exemplary embodiment may further include a light source module and a filter disposed in the solvent channel 1030 or the solvent storage 1010 to sterilize and purify the solvent 190.

FIG. 11 is a view of a fluid treatment device according to a tenth exemplary embodiment.

The fluid treatment device 10 according to the tenth exemplary embodiment may include a pipe 100, a fan 120, a first filter 130, light source modules 1051, 1052, 1053, and 1054, a second filter 1070, a solvent storage 1010, and a solvent channel 1030, and a circulation pump 1040.

The fluid treatment device 10 according to the tenth exemplary embodiment has a structure in which the second filter 1070 is added to the fluid treatment device 9 shown in FIG. 10. Here, the second filter 1070 has the same function as the second filter 670 of the fluid treatment device 6 shown in FIG. 6.

In this exemplary embodiment, the second filter 1070 may be disposed such that a side surface thereof closely contacts an inner surface of the pipe 100 defining the sterilization area S. Accordingly, the second filter 1070 may be disposed such that an upper surface thereof faces an upper inner wall of the pipe 100 with a space therebetween and a lower surface thereof faces a lower inner wall of the pipe 100 with a space therebetween.

The solvent 190 discharged from the solvent discharge portion 1020 passes through the second filter 1070 before falling to a bottom of the sterilization area S. Here, the second filter 1070 may adsorb contaminants trapped in the solvent 190. Accordingly, the solvent 190 having passed through the second filter 1070 may be in a state of being partially decontaminated by the second filter 1070.

According to this exemplary embodiment, the fluid treatment device 10 may include multiple light source modules 1050. For example, the multiple light source modules 1050 may include a first light source module 1051, a second light source module 1052, a third light source module 1053, and a fourth light source module 1054. Although the multiple light source modules 1050 are referred to as the first light source module to the fourth light source module 1051, 1052, 1053, 1054, respectively, this is merely for convenience of description and the first light source module to the fourth light source module 1051 to 1054 may have the same structure or different structures.

The first light source module 1051 may be placed at an upper portion of the sterilization area S to emit light in a downward direction. Thus, the first light source module 1051 may sterilize the fluid passing through the solvent 190. In addition, the first light source module 1051 may sterilize the solvent 190 falling in a state of trapping contaminants from the fluid therein. Further, the first light source module 1051 may sterilize contaminants trapped in the second filter 1070 placed below the first light source module 1051.

The second light source module 1052 and the third light source module 1053 may face each other on opposite inner surfaces of the pipe 100 defining the sterilization area S. In addition, the second light source module 1052 may be disposed close to the inlet 101 and the third light source module 1053 may be disposed close to the outlet 102.

The second light source module 1052 may emit light in the same direction as a flow direction of the fluid passing through the sterilization area S. In addition, the third light source module 1053 may emit light in a direction opposite to the flow direction of the fluid passing through the sterilization area S.

Accordingly, the fluid can be sterilized through continuous exposure to light from the second light source module 1052 and light from the third light source module 1053 while passing through the sterilization area S. The solvent 190 falling from the upper portion of the sterilization area S can also be sterilized by light from the second light source module 1052 and light from the third light source module 1053.

In addition, the second light source module 1052 may sterilize the fluid flowing from the inlet 101 toward the sterilization area S. The third light source module 1053 may sterilize the fluid flowing toward the outlet 102 through the sterilization area S.

Accordingly, the fluid treatment device 10 according to this exemplary embodiment can sterilize the fluid in the vicinity of the inlet 101 and the outlet 102, as well as the fluid within the sterilization area S. That is, the fluid treatment device 10 according to this exemplary embodiment can improve sterilization efficiency with respect to the fluid by repeatedly sterilizing the fluid moving therethrough.

The fourth light source module 1054 may be placed at the bottom of the sterilization area S to emit light in an upward direction.

Accordingly, the fourth light source module 1054 may sterilize contaminants trapped in the second filter 1070. In addition, the fourth light source module 1054 may sterilize the solvent 190 having passed through the second filter 1070.

When the fourth light source module 1054 is immersed in the solvent 190 as shown in FIG. 11, the fourth light source module 1054 may also sterilize the solvent 190 collected on the bottom of the sterilization area S.

The fluid treatment device 10 according to this exemplary embodiment can sterilize the solvent 190 and the second filter 1070, which serve to trap contaminants in the fluid, as well as the fluid. Accordingly, the fluid treatment device 10 according to this exemplary embodiment can keep the solvent 190 and the second filter 1070 clean. In this way, the solvent 190 and the second filter 1070 can retain the ability to trap contaminants, thereby improving sterilization efficiency of the fluid treatment device 10.

FIG. 12 is a view of a fluid treatment device according to an eleventh exemplary embodiment.

The fluid treatment device 11 according to the eleventh exemplary embodiment may include a pipe 1100, a fluid pump 1140, a support member 1160, and a light source module 1150.

According to this exemplary embodiment, the pipe 1100 may include a first pipe 1110, a second pipe 1120, and a third pipe 1130.

The first pipe 1110 may be formed at one end thereof with an inlet 1101 and the other end thereof may be connected to the second pipe 1120.

In addition, the first pipe 1110 may be provided with the fluid pump 1140.

The fluid pump 1140 may force fluid outside the fluid treatment device 11 to flow into the pipe 1100 through the inlet 1101.

The second pipe 1120 may be connected to each of the first pipe 1100 and the third pipe 1130.

Referring to FIG. 12, the second pipe 1120 may be connected at one end thereof to the first pipe 1110. Accordingly, the fluid introduced through the inlet 1101 by the fluid pump 1140 may flow into the second pipe 1120 through the first pipe 1110.

The second pipe 1120 may include a fluid discharge portion 1121. The fluid discharge portion 1121 is a passage through which the fluid introduced into the second pipe 1120 is discharged to the third pipe 1130.

Referring to FIG. 12, the fluid discharge portion 1121 may be provided in the form of multiple through-holes formed through the second pipe 1120. Alternatively, the fluid discharge portion 1121 may be provided in the form of multiple nozzles. As such, the fluid discharge portion 1121 may be any structure that can connect an interior of the second pipe 1120 to an interior of the third pipe 1130.

Referring to FIG. 12, the second pipe 1120 is disposed inside the third pipe 1130. However, the arrangement of the second pipe 1120 and the third pipe 1130 is not limited thereto. For example, in some exemplary embodiments, a fluid inlet (not shown) is formed through a lower surface of the third pipe 1130 such that the second pipe 1120 may be placed under the third pipe 1130. Here, the fluid discharge portion 1121 of the second pipe 1120 may be connected to the fluid inlet of the third pipe 1130 such that the interior of the second pipe 1120 can communicate with the interior of the third pipe 1130.

The third pipe 1130 may provide the sterilization area S.

At least one light source module 1150 may be disposed at an upper portion of the sterilization area S. Here, the light source module 1150 may be secured to the upper portion of the sterilization area S through the support member 1160.

The support member 1160 may be secured on at least one side surface thereof to an inner surface of the third pipe 1130. Here, the light source module 1150 may be disposed on a lower surface of the support member 1160 to emit light in a downward direction.

For example, the support member 1160 may include multiple through-holes through which the fluid passes. Alternatively, the support member 1160 may be provided in the form of a long rod to form a space between the support member 1160 and the inner surface of the third pipe 1130. As such, the support member 1160 is configured not to block a flow of the fluid from the sterilization area S to outlet 102. That is, the support member 1160 may be any structure that can form a passage through which the fluid can flow from the sterilization area S to the outlet 102 while allowing the light source module to be secured to a location between sterilization area S and the outlet 102.

The solvent 190 may be stored in the third pipe 1130 or the second pipe 1120.

Since the second pipe 1120 is disposed on the bottom of the third pipe 1130, the solvent 190 may be stored only in the second pipe 1120 or may be stored both in the second pipe 1120 and the third pipe 1130, depending on the quantity of the solvent 190.

According to this exemplary embodiment, external fluid may be introduced into the pipe 1100 through the inlet 1101 by the fluid pump 1140. The introduced fluid may move to the second pipe 1120 through the first pipe 1110 and then may be introduced into the sterilization area S in the third pipe 1130 through the fluid discharge portion 1121 of the second pipe 1120. Here, the fluid may be forced to pass through the solvent 190 stored in the second pipe 1120 by the fluid pump 1140. Here, the level of the solvent 190 can rise due to the quantity and force of the fluid.

The fluid can be decontaminated and purified while passing through the solvent 190.

Here, the fluid is introduced into the solvent 190 through the fluid discharge portion 1121, that is, the multiple through-holes. The fluid is split into multiple streams by the fluid discharge portion 1121 before passing through the solvent 190. Accordingly, a contact area between the fluid and the solvent 190 can increase, thereby allowing the solvent 190 to trap more contaminants from the fluid.

In addition, the fluid can be sterilized through exposure to light from the light source module 1150 while passing through the sterilization area S.

The solvent 190 with contaminants from the fluid trapped therein can also be sterilized by light from the light source module 1150.

Although not shown in this exemplary embodiment, the fluid treatment device 11 may further include a filter capable of filtering out contaminants in the fluid, such as a dust collection filter, in the first pipe 1110, as in other exemplary embodiments.

FIG. 13 is a view of a fluid treatment device according to a twelfth exemplary embodiment.

The fluid treatment device 12 according to the twelfth exemplary embodiment may include a pipe 1200, a fluid pump 1140, a support member 1160, a fluid discharge portion 1270, and a light source module 1150.

The fluid treatment device 12 according to this exemplary embodiment differs from the fluid treatment device 11 shown in FIG. 12, in that the second pipe is omitted and the first pipe 1110 and the third pipe 1130 are directly connected to each other.

Accordingly, the fluid introduced by the fluid pump 1140 may be directly introduced into the third pipe 1130 through the first pipe 1110.

The fluid introduced into the third pipe 1130 may be decontaminated and purified while passing through the solvent 190. In addition, the fluid having passed through the solvent 190 may be sterilized once more while passing through the sterilization area S and then may be discharged from the fluid treatment device 12 through the outlet 1102.

The fluid discharge portion 1270 may be provided to the third pipe 1130.

The fluid discharge portion 1270 may be placed above the solvent 190 across a region between the solvent 190 and the light source module 1150 placed at an upper portion of the sterilization area S.

The fluid discharge portion 1270 may include multiple through-holes allowing passage of the fluid therethrough. For example, the fluid discharge portion 1270 may have a mesh structure.

The fluid discharge portion 1270 serves to split the fluid passing therethrough into many streams. Accordingly, the fluid having passed through the fluid discharge portion 1270 comes into contact with the solvent 190 in a state of being split into many streams. Accordingly, a contact area between the fluid and the solvent 190 can increase, thereby allowing the solvent 190 to more efficiently trap contaminants.

The solvent 190 with contaminants from the fluid trapped therein can be sterilized by multiple light source modules 1150 disposed at the upper and lower portions of the sterilization area S.

FIG. 14 is a view of a fluid treatment device according to a thirteenth exemplary embodiment.

The fluid treatment device 13 according to the thirteenth exemplary embodiment may include a pipe 1200, a fluid pump 1140, a support member 1160, a fluid discharge portion 1370, and a light source module 1150.

The fluid treatment device 13 according to this exemplary embodiment differs from the fluid treatment device 12 shown in FIG. 13, in terms of the location of the fluid discharge portion 1370.

According to this exemplary embodiment, the fluid discharge portion 1370 is disposed between the first pipe 1110 and the third pipe 1130. Alternatively, the fluid discharge portion 1370 may be disposed at a portion of the first pipe 1110 at which the first pipe 1110 is connected to the third pipe 1130.

The fluid discharge portion 1370 may be formed to block the first pipe 1110. Here, the fluid discharge portion 1370 may include multiple through-holes allowing passage of the fluid therethrough. For example, the fluid discharge portion 1370 may have a mesh structure.

Accordingly, when the fluid is introduced into the third pipe 1130, the fluid is split into many streams by the fluid discharge portion 1370. Thus, the fluid split into many streams passes through the solvent 190, whereby a contact area between the fluid and the solvent 190 can increase.

The fluid treatment device 13 according to this exemplary embodiment can improve trapping efficiency of the solvent 190 by increasing the contact area between the fluid and the solvent 190. Accordingly, the fluid treatment device 13 according to this exemplary embodiment can improve sterilization efficiency.

FIG. 15 is a graph depicting sterilization efficiency of a light source module included in a fluid treatment device according to an exemplary embodiment.

According to this exemplary embodiment, the light source module may perform sterilization with different types of light depending on the type of contaminant, the purpose of use, the type of fluid, and the like.

For example, the light source module may be provided with a light source emitting UVC, UVB, or UVA depending on the sterilization purpose. In addition, the light source module may include a light source emitting light having a peak wavelength in the wavelength range of 400 nm to 430 nm depending on the sterilization purpose.

The light source of the light source module may be a light emitting diode.

FIG. 15 shows combinations of irradiation time and distance from the light source module that can achieve sterilization of about 99.9% of contaminants by UVC.

When the light source module emits UVC, 99.9% of contaminants within a distance of 30 cm from the light source module can be sterilized in about 4 seconds.

In addition, when the light source module emits UVC, 99.9% of contaminants within a distance of 50 cm from the light source module can be sterilized in about 11 seconds.

In addition, when the light source module emits UVC, 99.9% of contaminants within a distance of 70 cm from the light source module can be sterilized in about 22 seconds.

In addition, when the light source module emits UVC, 99.9% of contaminants within a distance of 100 cm from the light source module can be sterilized in about 45 seconds.

As such, the area over which sterilization is performed may also be increased in proportion to the sterilizing light irradiation time.

Accordingly, sterilization efficiency may be controlled by adjusting at least one of the amount of time the light source module emits light and the distance between the light source module and a contaminant.

Such a light source module may be the light emitting module applied to the first to thirteenth exemplary embodiments.

FIG. 16 is a view of a fluid treatment device according to an exemplary embodiment provided to a fluid treatment space.

Referring to FIG. 16, the fluid treatment device 14 is schematically shown. The fluid treatment device 14 shown in FIG. 15 may be one of the fluid treatment devices according to the exemplary embodiments described above.

The fluid treatment space 20 is placed outside the fluid treatment device 14 and may be a space 20 in which fluid flows or is stored. That is, the fluid may be a gas like air or a liquid like water. For example, the fluid treatment space 20 may be an indoor space requiring air purification.

In general, since a contaminant is heavier than air, the contaminant may be concentrated on the floor of the indoor space.

An inlet 1101 of the fluid treatment device 14 may be placed at a lower portion of the fluid treatment space 20.

In addition, the fluid treatment device 14 may be connected to an external duct 30. The external duct 30 may be connected to an outlet 1102 of the fluid treatment device 14 to discharge sterilized fluid to an upper portion of the fluid treatment space 20 therethrough.

When the outlet 1102 of the fluid treatment device 14 is formed to be located at the upper portion of the fluid treatment space 20, the external duct 30 may be omitted.

In addition, depending on where the fluid treatment device 14 is installed, the inlet 1101 and the outlet 1102 of the fluid treatment device 14 may be connected to the external duct, such that fluid in a lower region of the fluid treatment space 20 is introduced into the fluid treatment device 14 and sterilized fluid is discharged to an upper region of the fluid treatment space 20.

Accordingly, the fluid treatment device 14 according to the exemplary embodiment may perform sterilization after suctioning fluid from the lower region of the fluid treatment space 20, in which contaminants are concentrated, through a fan or a fluid pump. In addition, the fluid treatment device 14 may discharge sterilized fluid to the upper region of the fluid treatment space 20.

As such, the fluid treatment device 14 according to the exemplary embodiment is provided to the fluid treatment space to perform sterilization after suctioning contaminants concentrated on the floor of the fluid treatment space, thereby more efficiently sterilizing the fluid treatment space.

When sterilization of fluid is performed by directly irradiating moving fluid with light, it is difficult to secure sufficient time to complete sterilization of the fluid due to the speed at which the fluid moves.

Since the fluid treatment device according to the exemplary embodiments performs sterilization of fluid by separating contaminants from the fluid using the solvent stored in a specific region thereof, followed by sterilization of the solvent with the contaminants trapped therein, the fluid treatment device can provide improved sterilization efficiency, as compared with sterilization through direct exposure of fluid to light.

In addition, general filters may have insufficient trapping efficiency depending on the size of contaminants.

The fluid treatment device according to the exemplary embodiments uses the solvent, which is a liquid, so as to trap contaminants regardless of the size thereof. Accordingly, using the solvent, the fluid treatment device according to the exemplary embodiments can sterilize even contaminants difficult to trap using a general filter.

The fluid treatment device according to the exemplary embodiments can improve sterilization efficiency through increase in exposure time of contaminants in fluid to light having sterilization properties.

The fluid treatment device according to the exemplary embodiments can more efficiently sterilize a fluid treatment space by suctioning fluid from a lower region of the fluid treatment space, followed by sterilization of the fluid.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A fluid treatment device comprising:
a pipe having an inlet through which fluid is introduced into the pipe from a fluid treatment space, an outlet through which sterilized fluid is discharged to the fluid treatment space, and a flow channel connecting the inlet to the outlet, the pipe providing a sterilization area in the flow channel;
a solvent filling at least a portion of the sterilization area; and
at least one light source module disposed in the sterilization area, the light source module comprising a light source configured to emit sterilizing light and a substrate on which the light source is mounted,
wherein:
the fluid introduced through the inlet is configured to pass through the solvent towards the outlet;
the solvent is configured to trap contaminants contained in the fluid when the fluid passes through the solvent; and
the light source module is configured to sterilize the solvent having the contaminants trapped therein.

2. The fluid treatment device according to claim 1, wherein the light source module is disposed in at least one of a region inside the solvent and a region above the solvent.

3. The fluid treatment device according to claim 2, wherein the light source module is configured to sterilize at least one of the fluid passing through the solvent and the fluid having passed through the solvent.

4. The fluid treatment device according to claim 1, further comprising:
an inflow guide formed on an inner wall of the pipe and having one end placed inside the solvent to guide the fluid introduced through the inlet to flow into the solvent.

5. The fluid treatment device according to claim 1, further comprising:
at least one guide disposed in the sterilization area and having at least a portion placed inside the solvent to lengthen a flow path of the fluid.

6. The fluid treatment device according to claim 1, further comprising:
a filter placed inside the solvent and configured to trap or sterilize contaminants contained in the solvent and in the fluid passing through the solvent.

7. The fluid treatment device according to claim 6, wherein the light source module is configured to sterilize the contaminants trapped in the filter.

8. The fluid treatment device according to claim 1, further comprising:

a circulation member to force the solvent to flow.

9. The fluid treatment device according to claim 1, further comprising:

a solvent storage to store the solvent;

a solvent discharge portion configured to discharge the solvent from the solvent storage to the sterilization area; and a solvent channel through which the solvent discharged to the sterilization area moves to the solvent storage.

10. The fluid treatment device according to claim 9, wherein the solvent discharge portion is configured to discharge the solvent to the sterilization area in the form of a thin stream or a fine spray.

11. The fluid treatment device according to claim 9, further comprising:

a filter disposed between a bottom of the sterilization area and the solvent discharge portion to filter or sterilize contaminants contained in the solvent and in the fluid passing through the solvent.

12. The fluid treatment device according to claim 11, wherein the light source module is configured to sterilize the contaminants trapped in the filter.

13. The fluid treatment device according to claim 9, further comprising:

a fluid discharge portion through which the fluid introduced through the inlet is discharged into the solvent, wherein the solvent discharge portion is configured to split the fluid into multiple streams before the fluid is discharged into the solvent.

14. The fluid treatment device according to claim 1, wherein the fluid is configured to be introduced from a lower region of the fluid treatment space.

15. The fluid treatment device according to claim 1, wherein the sterilized fluid is configured to be discharged to an upper region of the fluid treatment space.

16. The fluid treatment device according to claim 1, further comprising:

at least one of a fan and a fluid pump to force the fluid to flow from the fluid treatment space into the inlet.

17. The fluid treatment device according to claim 1, further comprising:

a filter to filter the contaminants contained in the fluid before the fluid is introduced into the sterilization area.

18. The fluid treatment device according to claim 1, wherein the light source module further comprises a protective member covering the substrate and the light source to protect the substrate and the light source from the solvent, the protective member being formed of a light transmitting material.

* * * * *